United States Patent [19]
Clayberger et al.

[11] Patent Number: 5,888,512
[45] Date of Patent: Mar. 30, 1999

[54] LYMPHOCYTE ACTIVITY REGULATION BY HLA PEPTIDES

[75] Inventors: Carol A. Clayberger; Alan M Krensky, both of Stanford, Calif.

[73] Assignee: Board of Trustees of the Leland Stanford Junior University, Stanford, Calif.

[21] Appl. No.: 844,716

[22] Filed: Mar. 2, 1992

Related U.S. Application Data

[63] Continuation-in-part of Ser. No. 755,584, Sep. 3, 1991, abandoned, which is a continuation of Ser. No. 672,147, Mar. 19, 1991, abandoned, which is a continuation-in-part of Ser. No. 8,846, Jan. 30, 1987, abandoned.

[51] Int. Cl.⁶ ............... A61K 38/00; A61K 39/16; C07K 14/74
[52] U.S. Cl. ............ 424/185.1; 530/300; 530/324; 530/328; 530/868; 514/2; 514/12; 514/15
[58] Field of Search ................ 530/324, 325, 530/326, 327, 328, 329, 402, 403, 868; 514/2, 12–17; 424/184.1, 185.1, 193.1, 194.1

[56] References Cited

U.S. PATENT DOCUMENTS

| | | | |
|---|---|---|---|
| 4,634,590 | 1/1987 | Cohen et al. | 424/88 |
| 4,681,760 | 7/1987 | Fathman | 424/85.8 |
| 5,073,540 | 12/1991 | Olsson | 514/3 |
| 5,202,424 | 4/1993 | Vlassana et al. | 530/395 |
| 5,451,512 | 9/1995 | Apple et al. | 435/91.2 |

FOREIGN PATENT DOCUMENTS

| | | |
|---|---|---|
| WO 88/05784 | 8/1988 | WIPO . |
| WO 89/07448 | 8/1989 | WIPO . |
| 9010016 | 9/1990 | WIPO . |
| WO 90/10016 | 9/1990 | WIPO . |

OTHER PUBLICATIONS

Chen, et al., "Cytotoxic T Cell Recognition of an Endogenous Class I HLA Peptide Presented by a Class II HLA Molecule," *J. Exp. Med.* (1990) 172:779–788.

Rojo, et al., "HLA–B27 Antigenicity: Antibodies Against the Chemically Synthesized 63–84 Peptide from HLA–B27.1 Display Alloantigenic Specificity and Discriminate Among HLA–B27 Subtypes," *J. Immunol.* (1986) 137:904–910.

Raybourne, et al., "Monoclonal Antibodies Against an HLA–B27–Derived Peptide React with an Epitope Present on Bacterial Proteins," *J. Immunol.* (1990) 145:2539–2544.

Heath, et al., "Mapping of Epitopes Recognized by Alloreactive Cytotoxic T Lymphocytes Using Inhibition by MHC Peptides," *J. Immunol.* (1989) 143:1441–1446.

Clayberger, C. et al., *Current Opinion in Immunology* 7:644–648, "Immunosuppressive peptides corresponding to MHC Class I sequences", 1995.

W. F. Paul (ed.), *Fundamental Immunology*, 3rd edition, pp. 609–610. Raven Press, New York, 1993.

Bowie, J. U., et al., *Science* 247:130601310 (16 Mar. 1990), "Deciphering the message in protein sequences: tolerance to amino acid substitutions".

Alitalo, K., et al. (ed), *Synthetic peptides in biology and medicine*, Elsevier Science Publishers, New York (1985), pp. 191–197 by E. Ruoslahti, et al., "Synthetic peptides in the analysis of cell adhesion".

Koller et al; *Jo. of Immunol.* vol. 134, No. 4, Apr. 1985. pp. 2727–2733.

Vega et al; *P.N.A.S.* vol. 82, 1985, pp. 7394–7398.

Lopez de Castro et al; *Biochemistry* vol. 22, 1983, pp. 3961–3969.

Auffray et al., *J. Human Immunology* (1986) 15:381–390.
Biddison et al., *J. Immunol.*, (1980) 124(2):548–552.
Clayberger et al., *J. Exp. Med.* (1985) 163:1709–1714.
Cowan et al., *J. Immunol.* (1985) 135:2835–2841.
Duran et al., *Transplantation*, (1986) 41(3):279–285.
Gaston et al., *J. Exp. Med.* (1983) 158:280–293.
Holmes et al., *EMBO Journal*, (1985) 4:2849–2854.
Koller et al., *J. Immunol.* (1985) 134:2727–2733.
Krangel et al., *Biochemistry* (1982) 21:6313–6321.
Krangel et al., *J. Immunol.* (1983) 130:1856–1862.
Krangel et al., *J. Exp. Med.* (1983) 157:324–336.
Nathenson et al., *Ann. Rev. Immunol.* (1986) 4:471–502.
Parham et al., *Chemical Abstracts* (1987) 106:516, abstract No. 154384x.
Pease et al., *Proc. Natl. Acad. Sci.* (1983) 80:242–246.
Pierschbacher et al., *Nature* (1984) 309:30–33.
Salter et al., *J. Exp. Med.* (1987), 166:283–288.
Schulz et al., *Proc. Natl. Acad. Sci.* (1983) 80:2007–2011.
Spits et al., *Immunogenetics*, (1982) 16:503–512.
Taketani et al., *J. Immunol.* (1984) 133:816–821.
Towsend et al., (1986) *Cell*, (1986) 44:959–968.
Vega et al., *Proc. Natl. Acad. Sci.* (1985) 82:7394–7398.
Ways et al., *J. Biol. Chem.* (1985) 26:11924–11933.
Yamada et al., *J. Cell. Biol.* (1985) 28:99–104.

*Primary Examiner*—Thomas M. Cunningham
*Attorney, Agent, or Firm*—Morrison & Foerster LLP

[57] ABSTRACT

Fragments from the polymorphic domains of Class I HLA antigen domains are used to modulate T-cell activity. The peptides are from the α1- or α2 domains, particularly of the HLA-A, and B antigens. The peptides may be conjugated to other compounds to be used in diagnosis and therapy. The peptides may block lysis, CTL proliferation or have other regulating effects.

8 Claims, 5 Drawing Sheets

FIG. 4

LYMPHOCYTE ACTIVITY REGULATION BY HLA PEPTIDES

CROSS-REFERENCE TO RELATED APPLICATIONS

This application is a continuation-in-part of application Ser. No. 07/755,584, filed Sep. 3, 1991, now abandoned which is a continuation of application Ser. No. 07/672,147, filed Mar. 19, 1991, now abandoned, which is a continuation-in-part of application Ser. No. 07/008,846, filed Jan. 30, 1987, now abandoned.

INTRODUCTION

1. Technical Field

The field of this invention is the regulation of cytotoxic T-lymphocytes using peptide fragments from Class I HLA peptides.

2. Background

Cytotoxic T-cells, particularly cytotoxic T-lymphocytes ("CTL"), are restricted in their activity by recognizing a specific major histocompatibility complex ("MHC") antigen on the surface of the target cell, as well as a peptide bound in a cleft of the MHC antigen. The foreign antigen may be as a result of transplantation from an allogeneic host, viral infection, mutation, neoplasia, or the like. The involvement of the MHC protein appears to be essential to the attack by CTL's against the cell which includes the foreign antigen. The CTL's by monitoring the presence of foreign antigens, are able to destroy cells, which if otherwise allowed to proliferate, would result in the proliferation of pathogens or neoplastic cells.

In monitoring the presence of foreign antigens, the CTL's also recognize transplants of organs, tissue and cells, which come from allogeneic hosts. In order to protect the transplant from the CTL's, various immunosuppressive procedures are employed. These procedures are frequently unsatisfactory in not being completely protective and making the patient susceptible to opportunistic infection.

In view of the very great interest in being able to increase or decrease the numbers of CTL's and their activity, there is substantial opportunity for developing new techniques which would allow for regulating the CTL's, while still providing substantial protection against pathogens.

Relevant Literature

Clayberger, et al., *J. Exp. Med.* (1985) 11:1709–1714 describe HLA-A2 antigen in comparisons with HLA-Aw68 and Aw69. Townsend, et al., *Cell*, (1986) 44:959–968 suggests that CTL recognize segmental epitopes of denatured or degraded proteins in a similar way as helper T-cells. Holmes and Parham, *EMBO J.*, (1985) 4:2849–2854 describe the relationship of HLA-A2, Aw68 and Aw69. CTL target specificity has been taught to be extremely sensitive to changes in structure of human Class I molecules (Durna and Pease, *Transplantation*, (1986) 41:279–285: Biddison, et al., *J. Immunol.*, (1980) 124:548–552: Spits, et al., *Immunogenetics*, (1982) 16:503–512: Gaston, et al., *J. Exp. Med.* (1983) 158:280–293).

Mutants which affect recognition by CTL have been studied in mice (Nathenson, et al., *Ann. Rev. Immunol.* (1986) 4:471–502: Schulz, et al., *Proc. natl. Acad. Sci. USA* (1983) 80:2007–2011) and humans, (Krangel, *Biochemistry* (1982) 21:6313–6321: Krangel, et al., *J. Immunol.* (1983) 130:1856–1862: Cowan, et al., *J. Immunol.* (1985) 135:2835–2841: Taketani, et al., ibid (1984) 133:816–821; and Vega, et al., *Proc. Natl. Acad. Sci. USA* (1985) 82:7394–7398).

These reports have focused considerable attention on the region between residues 147 and 157, although other regions can also produce functional differences (Ezquerra, et al., *J. Immunol.* (1985) 134:2727–2733). Clusters of variability have been reported at the carboxy-terminal end of the first extracellular domain and at the amino-terminal end of the second extracellular domain (Ways, et al., *J. Biol. Chem.* (1985) 26:11924–11933). Sequences between residues 105–108 of all Class I molecules are related to that of the fibronectin binding tetrapeptide (Auffray and Novotny, *J. Human Immunology* (1986) 15:381–390), which tetrapeptide in either orientation is found to have cell attachment properties (Pierschbacher and Ruoslahti, *Nature* (1984) 309:30–33; Yamada and Kennedy, *J. Cell. Biol.* (1985) 28:99–104). Substitution at position 107 affecting a single monoclonal antibody defined epitope of HLA-A2 has been reported by Salter, et al., *J. Exp. Med.* (1987) 166:283–288.

SUMMARY OF THE INVENTION

Methods and compositions are provided based on the sequence of Class I antigen α1- and α2-domains. These fragments include at least a portion of the amino acids between positions 55 and 120 of the Class I antigens and are used for modulating cytotoxic T-lymphocyte ("CTL") activity toward target cells. Different peptides may elicit different effects in relation to CTL's or subsets of CTL's.

BRIEF DESCRIPTION OF THE DRAWINGS

FIG. 4 shows the consensus sequence of peptides which constitute the α1, α2 and α3 regions of a Class I HLA molecule, as well as changes in these sequences in different specific HLA molecules.

DESCRIPTION OF THE SPECIFIC EMBODIMENTS

Figure 1:
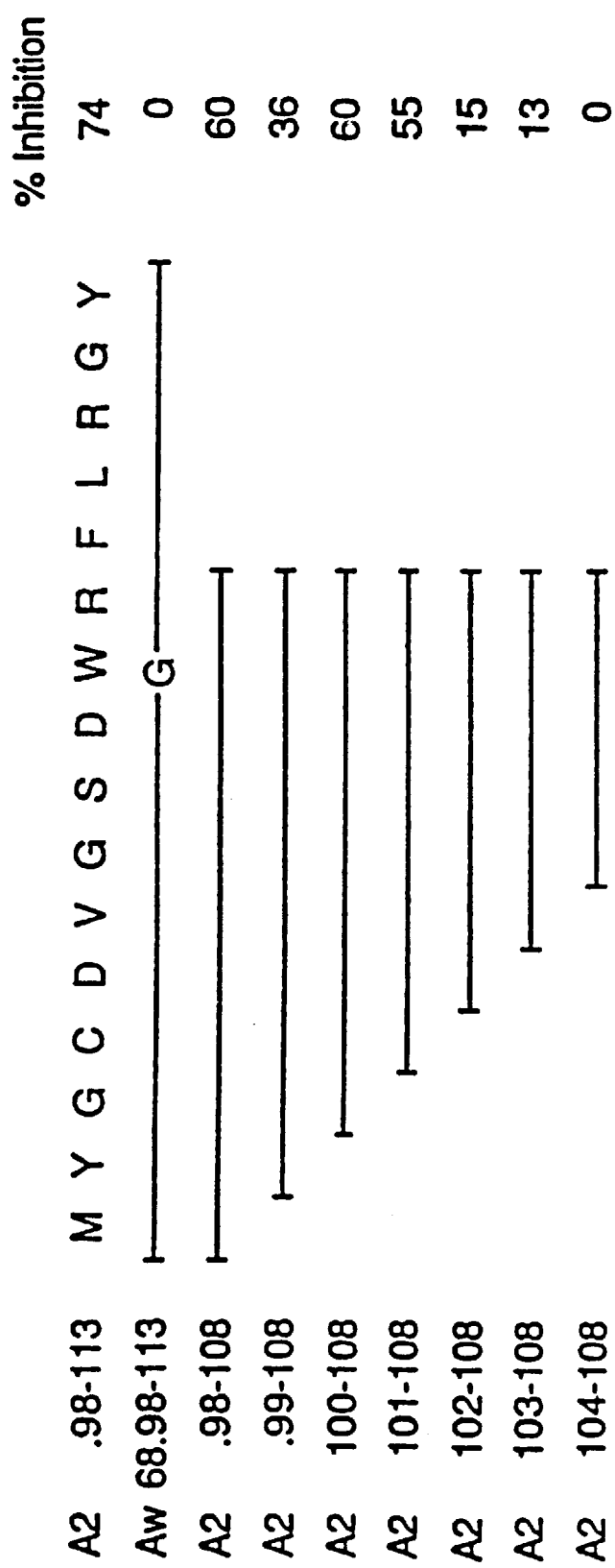
FIG. 1 shows the minimum size of peptide sequence required for inhibition of cytolysis by HLA-A2 specific CTL.

In accordance with the subject invention, CTL activity in a patient is modulated by administering to the patient a sequence of the polymorphic region of Class I major histocompatibility complex antigens, of the host. The polymorphic region comprises the α1- and 60 2-domains, with the α1-domain being of particular interest. The Class I antigens in the human are designated A, B and C, of which the A and B antigens are of particular interest.

Besides modulating the activity of CTL's, the subject peptides may also be used for identifying CTL's which bind to the particular peptide, removing particular subsets of CTL's from a T-cell composition or portion thereof and the like. For the most part, the subject compositions will comprise pure compositions or formulated compositions of a peptide of at least 8 amino acids, usually at least 12 amino acids, having a sequence coming within the extended sequence and up to the entire extended sequence:

$aa^{55}$ G P E Y W D $aa^{62}$ $aa^{63}$ T $aa^{65}$ $aa^{66}$ $aa^{67}$ K $aa^{69}$ $aa^{70}$ $aa^{71}$ Q T $aa^{74}$ R $aa^{76}$ $aa^{77}$ L $aa^{79}$ $aa^{80}$ $aa^{81}$ $aa^{82}$ $aa^{83}$ Y

Y N Q S E A G S H aa$^{94}$ aa$^{95}$ Q aa$^{97}$ M aa$^{99}$ G C D aa$^{103}$ G aa$^{105}$ D aa$^{107}$ R aa$^{109}$ L R G aa$^{113}$ aa$^{114}$ Q aa$^{116}$ A Y D G (Seq. ID No:10)

wherein:
- aa$^{55}$ is E or K, particularly E;
- aa$^{62}$ is G, Q, E or R, particularly R or G;
- aa$^{63}$ is an acidic amino acid or amide thereof, particularly E;
- aa$^{65}$ is Q, R or G, particularly Q or R;
- aa$^{66}$ is I, N or K, particularly I or K;
- aa$^{67}$ is an aliphatic neutral or Y amino acid, particularly C, S, V or Y;
- aa$^{69}$ is an aliphatic neutral or basic amino acid, particularly A, R or T;
- aa$^{70}$ is Q, H, S, N or K;
- aa$^{71}$ is an aliphatic neutral amino acid, particularly A, L, S or T;
- aa$^{74}$ is D, Y or H;
- aa$^{76}$ is E or V;
- aa$^{77}$ is D, S or N;
- aa$^{79}$ is R or G;
- aa$^{80}$ is T, I or N;
- aa$^{81}$ is an aliphatic non-polar amino acid, particularly A or L;
- aa$^{82}$ is R or L;
- aa$^{83}$ is G or R;
- aa$^{94}$ is T or I;
- aa$^{95}$ is a non-polar aliphatic amino acid of from 5 to 6 carbon atoms;
- aa$^{97}$ is an aliphatic amino acid or W;
- aa$^{99}$ is an aromatic amino acid;
- aa$^{103}$ is a non-polar aliphatic amino acid of from 5 to 6 carbon atoms;
- aa$^{105}$ is P or S;
- aa$^{107}$ is G or W;
- aa$^{109}$ is L or F;
- aa$^{113}$ is Y or H;
- aa$^{114}$ is H, Q, D, N or R;
- aa$^{116}$ is Y, D, S, F or H, which modulates CTL activity.

A subset of peptides of particular interest come within the following extended sequence:

G S H $aa^{94}$ $aa^{95}$ Q $aa^{97}$ M $aa^{99}$ G C D $aa^{103}$ G $aa^{105}$ D $aa^{107}$ R $aa^{109}$ L R G $aa^{113}$ $aa^{114}$ Q $aa^{116}$ A Y D G Residues 36–65 of Seq. ID No:10 wherein:

$aa^{94}$ is T or I;

$aa^{95}$ is a non-polar aliphatic amino acid of from 5 to 6 carbon atoms;

$aa^{97}$ is an aliphatic amino acid or W;

$aa^{99}$ is an aromatic amino acid;

$aa^{103}$ is a non-polar aliphatic amino acid of from 5 to 6 carbon atoms;

$aa^{105}$ is P or S;

$aa^{107}$ is G or W;

$aa^{109}$ is L or F;

$aa^{113}$ is Y or H;

$aa^{114}$ is H, Q, D, N or R;

$aa^{116}$ is Y, D, S, F or H.

Another subset of sequences coming within the above-extended sequence of particular interest are sequences coming within the extended sequence:

$aa^{55}$ G P E Y W D $aa^{62}$ $aa^{63}$ T $aa^{65}$ $aa^{66}$ $aa^{67}$ K $aa^{69}$ $aa^{70}$ $aa^{71}$ Q T $aa^{74}$ R $aa^{76}$ $aa^{77}$ L $aa^{79}$ $aa^{80}$ $aa^{81}$ $aa^{82}$ $aa^{83}$ Y Y N Q S E A Residues 1–35 of Seq. ID No:10 wherein:

$aa^{55}$ is E or K, particularly E;

$aa^{62}$ is G, Q, E or R, particularly R or G;

$aa^{63}$ is an acidic amino acid or amide thereof, including E and N, particularly E;

$aa^{65}$ is Q, R or G, particularly Q or R;

$aa^{66}$ is I, N or K, particularly N or K;

$aa^{67}$ is an aliphatic neutral amino acid including V, M, S, C and Y, particularly V;

$aa^{69}$ is an aliphatic neutral amino acid including A, T and P, particularly A;

$aa^{70}$ is Q, H, S, N or K, particularly Q or H;

$aa^{71}$ is an aliphatic neutral amino acid including S, A and T, particularly S;

$aa^{74}$ is D, Y or H, particularly D or H;

$aa^{76}$ is E or V;

$aa^{77}$ is D, S or N, particularly D;

$aa^{79}$ is R or G, particularly G;

$aa^{80}$ is T, I or N, particularly T or I;

$aa^{81}$ is an aliphatic non-polar amino acid including L or A, particularly L;

$aa^{82}$ is R or L, particularly R;

$aa^{83}$ is G or R, particularly G.

Another series of peptides of at least 8 amino acids of particular interest come within the extended sequence:

Q E G P E Y W D (G or R) (E or N) T (R or Q) (K or N) V K A (H or Q) S Q T (H or D) R (V or E) (D, S or N) L (G or R) (T or I) (L or A) (R or L) (G or R) Y Y N Q S E A.

Other extended sequences from which 8 amino acid fragments are of interest include:

T L Q R M Y G C D V G S D W R F L R G Seq. ID No:11,

M Y G C D V G S D W R F L R G Y Seq. ID No:12,

M Y G C D V G S D G R F L R G Y Seq. ID No:13,

G P E Y W D G E T R K V K A Seq. ID No:14,

W D R E T Q I C K A K A Q T D R N (N or D) L R (I or T) (A or L) L R Y Y Seq. ID No:15,

W D R E T Q K Y K R Q A Q T D R V S L R N L R G Y Seq. ID No:7,

W D R E T Q I S K T N T Q T Y R E S L R N L R G Y Seq. ID No:8, and

W D G E T R K V K A H S Q T H R V D L G T L R G Y Seq. ID No:16.

Of particular interest are the shorter sequences:

R E N L R I A L R Y Seq. ID No:3;

R E D L R T L L R Y Seq. ID No:17; and

W D R E T Q I C K A Seq. ID No:18.

Among the sequences of interest are the sequences in the α1-domain, namely the amino acid sequence from positions 55–85, more particularly 55–80 or 70–85, desirably including within the sequence a tetrapeptide DGET, GETR, DRAT, YWDG, RE(N or D)L or (A or L)LRY. Of particular interest for the α2-domain is the amino acid sequence from positions 90–112, more particularly 94–116, desirably including within the sequence a tetrapeptide STWR or SDGR.

The peptides of interest which will serve as the receptor binding peptide will have at least 8 amino acids, usually at least 10 amino acids, more usually at least 12 amino acids, frequently having 15 or more amino acids, and usually not more than about 30 amino acids, more usually not more than about 24 amino acids, desirably having about 12 to 21 amino acids. The amino acid sequence will usually not differ from a naturally occurring sequence by more than 2 amino acids, or mutations, e.g. deletions or insertions, more usually by not more than about 1 amino acid. The sequence employed will usually be from the polymorphic regions of the C-terminal half of the α1 domain or the N-terminal half of the α2 domain of the MHC antigen of the host of the MHC restricted T-cells, particularly an HLA-A or -B group antigen.

Of particular interest is a sequence or sequence fragment of at least 8 amino acids of the sequence:

G S H T (V, I or L) Q R M Y G C D V G S D (W or G) R F L R G Y H Q Y A Y D G Seq. ID No:19.

Where there are two or more amino acids indicated at the same site, any of the indicated amino acids may be present.

The region of particular interest will be the region from amino acid positions 110 to 116.

The subject peptides may be modified in a wide variety of ways. The peptides may be joined by covalent bonds at any convenient site along the peptide to a variety of other compounds for different purposes. Thus, the peptides may be joined to immunogens for administration to a host for immunization for production of antibodies, or may be joined to a non-adjacent MHC sequence of the particular MHC antigen by means of synthesis, expression of a synthetic gene, or the like; joined to a lipid or polyalkyleneoxy group; joined to a sugar; or joined to a nucleic acid. Of particular interest is joining the subject peptides to another peptide by synthesis or expression of a synthetic gene where the other peptide provides for extended stability of the subject peptides when administered to a host. Various peptides may be used, such as the immunoglobulin constant region, e.g. IgGFc. Alternatively, the subject peptides may be joined to a toxin, such as diphtheria toxin, ricin, abrin, etc., particularly where the binding chain has been removed or inactivated, so as to prevent binding of the binding chain to cells.

The subject peptides may be joined together to provide a single polypeptide having a multiplicity of activities or may be combined in a mixture to provide the same general activity.

The classes of amino acids are designated as follows:

aliphatic
- non-polar G, A, P, L, I, V polar
  - neutral C, S, T, M, N, Q
  - acidic D, E
  - basic K, R aromatic F, H, W, Y The peptides may be prepared in a variety of ways. Conveniently, they can be synthesized by conventional techniques employing automatic synthesizers, such as the Beckman, Applied Biosystem Inc., or other useful peptide synthesizer apparatus, or may be synthesized manually. Alternatively, DNA sequences can be prepared which encode the particular peptide and may be cloned and expressed to provide the desired peptide. In this instance a methionine may be the first amino acid.

The peptides may also be isolated from natural sources and purified by known techniques, including, for example, chromatography on ion exchange materials, separation by size, immunoaffinity chromatography and electrophoresis. As used herein, the term "a substantially pure preparation of peptide compound" means a preparation of the peptide which is usually greater than about 70% free of materials with which the polypeptide is naturally associated, and preferably greater than about 80% free of these materials; these materials, however, exclude materials with which the peptide may be mixed in the preparation of pharmaceutical compositions. The sequences may be modified in a variety of ways depending upon their ultimate purpose. Different N- or C-terminal groups may be introduced which allow for linking of the peptide to solid substrates or other molecules. In a synthetic procedure, any molecule may be introduced at the N- or C-terminus which would allow for subsequent reaction, depending upon the purpose for which the peptide is prepared.

For diagnostic purposes, a wide variety of labels may be linked to the terminus, which may provide, directly or indirectly, a detectable signal. For example, fluorescers may be introduced at the terminus or other molecules which provide a linkage to labels such as fluorescers, enzymes, particles, or the like. For example, linkage may be introduced at the terminus, e.g., biotin, which will bind to an avidin conjugate with enzymes or fluorescers. Alternatively, various reactive sites may be introduced at the terminus for linking to particles, solid substrates, macromolecules, or the like. For example, an internal amino moiety of a growing chain bound to a solid substrate with the intermediate side groups protected, may be conjugated with methyldithiobenzoic acid (MDTB). The free mercaptan group may then be used for conjugating with activated olefins. Thus, proteins, such as serum albumin, keyhole limpet hemocyanin, bovine β-globulin, or the like, may be conjugated to the peptide to provide for an immunogen to produce antibodies to the peptide for use in immunoassays, for affinity chromatography, or the like. Alternatively, the peptide can be bonded to another polypeptide by preparing a DNA sequence which has the peptide at the N-terminus, C-terminus or internal to the protein, so as to provide a fused protein which includes the binding peptide of interest. In this manner, fused proteins may be produced which have enzymatic activity, which enzymatic activity may be modulated by macromolecules, e.g., antibodies, binding to the peptide of interest. Thus, the peptides of the subject invention may be modified in a wide variety of ways for a variety of end purposes while still retaining biological activity.

The subject peptides may also be used in combination with antigenic peptides or proteins of interest to activate CTL's. Thus, the subject peptides may be bound to a protein, either directly or indirectly, so as to be able to present two epitopes to the CTL to which the CTL may bind and be activated. Of particular interest, is where the subject peptides may be bound to a liposome or a bilayer lipid membrane in conjunction with a peptide or protein providing the other determinant site.

Various techniques are available for joining a peptide or protein to a lipid, particularly a phospholipid to provide for the presence of the peptide or protein on the liposome surface. Phosphatidyl choline, phosphatidyl ethanolamine, or other lipid may be used with a bifunctional linking agent, such as MBSE, glutaraldehyde, methyldithiobenzoic acid, or the like. The formation of liposomes with conjugated proteins finds ample support in the literature, see, for example, U.S. Pat. Nos. 3,887,698; 4,261,975 and 4,193,983. The modified peptide or protein is combined with the lipids in an aqueous medium and sonicated to provide the desired liposomes. The liposomes may then be harvested and used in the ways indicated.

The subject peptides, by themselves, or in combination with other peptides or proteins, may be used for diagnosing the presence of CTL's which bind to a subject peptide or the combination of a subject peptide and other peptide or protein. In this manner, conjugates of the subject peptide and the antigenic peptide or protein can be prepared by employing linking agents as described previously. Alternatively, the subject peptide and the antigenic peptide may be bound to a solid surface, such as a particle, container surface, or the like. If desired, the subject peptide and antigenic peptide or protein may be conjugated to a particle or protein which is fluorescent. The binding of the particle or protein will allow for sorting and counting in a fluorescence activated cell sorter.

The subject peptides may also be used for modulating CTL activity in the mammalian host. The modulation may be by inhibiting CTL activity or by sensitizing target cells. This can be achieved by employing apheresis, where the patient's blood is withdrawn from the patient and circulated through a device in which the peptide is present, either bound to the surface, to remove CTL's active with the subject peptide or in a physiologically acceptable medium to bind to the CTL's and inhibit their activity. Alternatively, the subject peptides may be administered to a host intravascularly, in either an artery or vein, to provide for inhibition or stimulation of the CTL.

Examples of inhibitory peptides are presented infra (see Examples 2 and 9), which are derived from both the $\alpha_1$ and $\alpha_2$ domain of HLA-A2. In each case the sequence of the inhibitory peptide correlates with the epitope specificity of the CTL. Moreover, as shown in Example 4, inhibition is mediated by an octapeptide, and occurs by peptide binding to the CTL and not the target cell (see Example 5). Since the inhibitory capacity of the individual peptides correlates with CTL specificity, it seems likely that these peptides inhibit by binding to the variable T cell receptor.

An example of a peptide which stimulates cytolysis of HLA-Class I bearing target cells by alloreactive CTL is presented in Example 10, infra. The simplest interpretation of the results in Examples 10–12 is that the HLA-A2/B17 specific CTL recognize the A2 56-69 peptide in the context of HLA-Aw69 as a restriction element. This implies that the peptide is binding to the HLA-Aw69 molecule. The data and interpretation are similar to those obtained in the influenza (Bastin et al., *J. Exp. Med.,* 165:1508 (1987); Gotch et al., *Nature* 326:881 (1987)) and xenogeneic systems (Maryanski et al., *Nature* 324:578 (1986)), and demonstrate that alloreactive CTL can recognize Class I derived peptides in a Class I restricted fashion. However, the quantities of peptide required to cause sensitization are significantly larger than those reported in other studies. Although the molecular basis for this is as yet unknown, one possible explanation involves the relative handling of exogenous versus endogenous molecules. For example, HLA is an endogenous molecule, and the exogenous HLA peptides may have to compete with endogenous HLA peptides. Another alternative is that the A2.56-69 peptide may not include all of the residues required for high affinity binding to the target cell.

Two of the CTL epitopes from which the peptides described in the Examples, infra. are derived, are situated in very different parts of the HLA-A2 molecule. Residues 62–65 are in an alpha helix which forms part of the peptide binding site (Bjorkman et al., *Nature* 329:506 (1987)), which is itself thought capable of binding alpha helical peptides. As shown in the Examples, peptides in this region can either inhibit or induce cytolysis. In the induction of cytolysis, it is possible that the peptide may bind to a target cell HLA Class I antigen and thereby create a structure which is recognized by the CTL. For example, in the case of A2.56-69 peptide conferring sensitivity to clone A2/B17 cells on HLA-Aw69 cells, the bound peptide presumably substitutes for the $\alpha$ helix of the $\alpha_1$ domain, since HLA-Aw69 and HLA-A2 have identical $\alpha_2$ domains.

In contrast, residue 107 is part of a turn between two strands of $\beta$ structure at some distance from the alpha helices and peptide binding region (Bjorkman et al., supra.) The A2.98-113 peptide may maintain elements of this structure in solution and have little affinity for the peptide binding site of Class I molecules. This interpretation would explain the observation in the Examples that peptides corresponding to this region are inhibitors of HLA-A2 directed cytolysis, but cannot induce cytolysis.

The various activities of the peptides may be determined by appropriate assays. Inhibition of CTLs by peptides may be determined by employing CTL lines specific for a particular HLA in a target cell line carrying the target HLA. The target cell line is labeled, for example, with $^{51}$Cr. These cells are combined in an appropriate medium and the release of the label determined as indicative of the degree of cytolysis. The peptide may be added at the same time as the cells are brought together, may be incubated with the CTLs or may be incubated with the target cell to investigate the mode of action of the peptide.

Instead of using an exogenous marker, one may determine the release of serine esterase activity upon combining the CTLs and the target cells in conjunction with the peptide. The presence of serine esterase activity can be related to the release of granules.

As already indicated, the peptide may be present by itself, or in combination with an antigen thereby providing a different determinant site of interest. Depending upon whether only the subject peptide is included, or the peptide in combination with other peptides, activation or inhibition can be achieved. If irreversible inhibition is desired, the conjugate of the subject peptide with the antigen may be joined to a cytotoxic agent, joined to liposomes containing cytotoxic agents, or joined to a specific monoclonal antibody or immunoglobulin, whereby binding of the conjugate to the CTL will result in the complement mediated lysis of the CTL.

In addition, specific peptides may also serve to block differentiation of CTL, which blocking may be specific or non-specific. The subject peptides may also be used to modulate CTL activity, wherein modulation includes inhibiting cytolytic activity, where the inhibition may be reversible or irreversible. In some instances, the subject peptides may be used for determining the presence of particular sets or subsets of MHC-restricted CTL's.

These various capabilities may be achieved by combining cellular compositions comprising CTL's with the peptide in sufficient amount to provide the desired property. Where separation is desired, affinity columns, conjugated beads, e.g. magnetic beads, or other technique may be used, where the peptide-bound cells may be separated from other cells which are either not bound or non-specifically bound.

The subject peptides, by themselves or as conjugates, may be prepared as formulations in pharmaceutically acceptable media, for example saline, PBS, and glucose, generally at a pharmacologically effective dose, the concentrations of which will be determined empirically in accordance with conventional procedures for the particular purpose. The additives may include bactericidal agents, stabilizers, buffers, or the like. The amount administered to the host will vary depending upon what is being administered, the purpose of the administration, such as prophylaxis or therapy, whether inhibition or activation is desired, the state of the host, the manner of administration, and the like. In order to enhance the half-life of the subject peptide or subject peptide conjugates, the peptides may be encapsulated, introduced into the lumen of liposomes, prepared as a colloid, or other conventional technique may be employed which provides an extended lifetime of the peptides.

The following examples are offered by way of illustration and not by limitation.

EXAMPLES

Example 1
Preparation of Peptides Derived From HLA-A2

Four peptides were prepared by conventional synthetic methods using standard solid-phase methods. See Erickson & Merrifield in: *The Proteins* Vol. 2, 3rd edition (eds. Neurath, H. & Hill, R. L.) p. 255–527 (Academic Press, N.Y. 1970), which is hereby incorporated herein by reference. Three of the peptides had amino acids from the $\alpha_2$ domain and one of the peptides had amino acids from the $\alpha_2$ domain of a HLA-A2 antigen. The four peptides had the following compositions and designations:

A2.56-69 G P E Y W D G E T R K V K A Seq. ID No:20

A2.94-112 T L Q R M Y G C D V G S D W R F L R G Seq. ID No:11

A2.98-113 M Y G C D V G S D W R F L R G Y Seq. ID No:12

Aw.68 98-113 M Y G C D V G S D G R F L R G Y Seq. ID. No:13

The designations indicate the major histocompatibility antigen from which the peptide is derived, and the position of the amino acids in the antigen.

Example 2
Inhibition of HLA-A2 Specific CTL by Peptides Derived from HLA-A2.98-113 and HLA-A2.94-112

Peptides prepared as in Example 1, i.e., those corresponding to HLA-A2.56-69, HLA-A2.94-112, HLA-A2.98-113, and HLA-Aw 68.98-113, were preincubated for 30 min. with 1–3×10³ CTLs before addition of 10³ CPM of $^{51}$Cr-labeled B-lymphoblastoid target cells. The cytotoxicity assay was then performed as described by Clayberger et al., *J. Exp. Med.* (1984) 162:1709–1714; and Reiss et al., *Proc. Natl. Acad. Sci. USA* (1980) 77:5432–5436, which are hereby incorporated herein by reference.

In the first study, the CTL cell line was AJY, a long term CD8⁺ CTL line specific for HLA-A2, and the target cell was the B-lymphoblastoid cell line JY (HLA-A2, B7). In the second study the CTL was PWSB, a bulk culture with reactivity against HLA-B17 and the target was FMB, which expresses HLA-A1, A32, B17. In each case the percentage of specific release obtained in the absence of peptide was determined. The lower amount of specific release in the second study potentially made cytolysis more sensitive to inhibition. Stocks of peptides at 1 mg/ml in PBS were diluted to give final concentrations in the assay as indicated in Table 1. As a control inhibitor, the monoclonal antibody PA2.6 which is directed against the monomorphic determinant of HLA-A, B, 6 molecules was used (Reiss et al., supra: McMichael, *J. Exp. Med.* (1980) 152:195s–203s). The peptides employed were A2.98-113, A2.94-112, Aw68.94 112 and A2.56-69. The following table indicates the results.

TABLE 1

| | | % Specific Lysis | | | |
|---|---|---|---|---|---|
| Concentration | μg/ml | A2.98–113 | A2.94–112 | Aw68.94–112 | A2.56–69 |
| Trial 1. | 160 | 0 | 3 | 52 | 51 |
| CTL = AJY | 80 | 4 | 20 | 45 | 3.8 |
| Target = JY | 40 | 18 | 35 | 63 | 61 |
| Trial 2. | 160 | 27 | 35 | 28 | 20 |
| CTL = PWSB | 80 | 29 | 32 | 30 | 27 |
| Target = FMB | 40 | 30 | 34 | 35 | 31 |

In the first case, the percentage specific release-obtained in the absence of peptide was about 54, while in the second case it was about 28.

The above results with CTL which are restricted by the HLA-A2 antigen, show inhibition of specific cytotoxicity. With CTL's not restricted by A2, lysis of random target cells occurs with the results approximating the standard specific release obtained in the absence of peptide. These results suggest that the tryptophan at position 107 may be critical. Peptide A2.98-113 and peptide Aw68.98-113 are homologous except for the substitution of glycine for tryptophan at this position; this substitution resulted in a loss of inhibition of cytolysis by HLA-A2 specific CTL.

The results of treatment of peptide A2.98-113 with different proteases, i.e., trypsin or chymotrypsin, allow the suggestion that arginine 108 is of importance, but that peptides 109–113 are not critical. The major sites of action of trypsin and chymotrypsin are Arg, Lys, and Trp, Phe, Tyr, respectively. Chymotryptic, but not tryptic, cleavage of the peptide reduced the inhibitory activity (results not shown).

Example 3

Effect of Specificity of CTL and Target Cell on Inhibition of Cytolysis Caused by HLA-Derived Peptides A number of different CTL cell lines were studied, where the specificity of the cell lines were varied. The results shown in Table 2 indicate that only where the CTL's and the target cells share A2 specificity do the A2-derived peptides provide inhibition.

TABLE 2

Specificity of CTL Tests for Inhibition by Peptides

| CTL | Specificity of CTL | Target Cell | Target Molecule | Inhibition of Lysis by Peptide | | | |
|---|---|---|---|---|---|---|---|
| | | | | A2.98–113 | A2.94–112 | Aw68.98–113 | A2.56–69 |
| Line AJY | A2 | JY | A2 | + | + | − | − |
| Line PJY | A2 | JY | A2 | + | + | − | − |
| Clone A20.1 | A2 | JY | A2 | + | + | − | − |
| Clone AI.10 | A2 | JY | A2 | + | + | − | − |
| Clone AI9.1 | A2,Aw68,Aw69 | JY | A2 | + | + | − | − |
| Line PWSB | A2,B17 | JY | A2 | + | + | − | − |
| Line PWSB | A2,B17 | FMB | B17 | − | − | − | − |
| Clone AL8.1 | Aw68,Aw69 | LB | Aw68 | − | − | − | ND |
| Clone A15.1 | Aw69 | IDF | Aw69 | − | − | − | ND |
| Line CJY | Dr6 | Jy | DR6 | − | ND | − | − |
| Line CJY | Dr6 | DAUDI | Dr6 | − | ND | − | − |

The specificity of the CTL is based upon analysis of the pattern of killing on a panel of B lymphoblastoid cell lines and by patterns of inhibition with monoclonal antibodies. ND indicates not done. CTL used were from four different donors.

Example 4

Minimum Peptide Sequence Required for Inhibition of HLA-A2 Specific CTL

The minimum peptide sequence required for inhibition of cytolysis by HLA-A2 specific CTL was determined by examining the effect of size on the inhibition.

A series of peptides which started at positions 98–104 and ended at position 108 of HLA-A2 or HLA-Aw68 were synthesized. The effect of these peptides on cytolysis of JY cells (HLA-A2, B7, DR4,6) by seventeen different HLA-A specific lines or clones were tested. The HLA-A2 specific lines or clones were generated as described in Clayberger et al., supra. Peptides (200 mg/ml) were preincubated with 1–3×10$^3$ CTL for 30 minutes prior to addition of 10$^3$ CPM of $^{51}$Cr-labeled target cells. The peptides were present throughout the cytotoxicity assay which was performed as described in Clayberger et al., supra, and in Krensky et al., Proc. Natl. Acad. Sci. USA 79:2365 (1982), which are hereby incorporated herein by reference. Peptides were prepared as stock solutions at 1 mg/ml in phosphate buffered saline and diluted in complete medium (MEN supplemented with 10% calf serum) to give the final concentration used.

The results on the inhibition of cytolysis by CTL-A2 is shown in FIG. 1A, where inhibition is expressed as (1-[specific cytolysis in the presence of peptide/specific cytolysis in the absence of peptide])×100.

As seen in the figure, peptide 104–108 did not inhibit, peptides 102–108 and 103–108 caused weak inhibition, and the remaining peptides caused good inhibition of cytolysis. Thus, an octapeptide comprising residues 101–108 was sufficient to cause the inhibitory effect. A major decrease in the inhibitory effect occurs with loss of the cysteine at position 101. This loss may be due to the loss of disulfide cross-linking of two peptide molecules when cysteine 101 is absent.

Example 5

Locus of Action of Peptide A2.98-113

The locus at which peptide A2.98-113 interacts to cause an inhibitory effect on HLA-A2 specific CTL mediated cytolysis, i.e., with the CTL and/or with the target cell, was determined as follows.

The CTL (1×10$^6$ CTL-A2) and/or the target cells ($^{51}$Cr-labeled JY target cells) were incubated with 100 μg of A2.98-113 for 30 min. at 37° C., or alternatively with the control peptide, Aw68.98-113. The sequences of these peptides are presented in Example 1. As an additional control, the cells were incubated with complete medium minus peptide. Following the incubation, the cells were washed three times in complete medium, and tested in a $^{51}$Cr-release assay (see Example 2).

Figure 2:
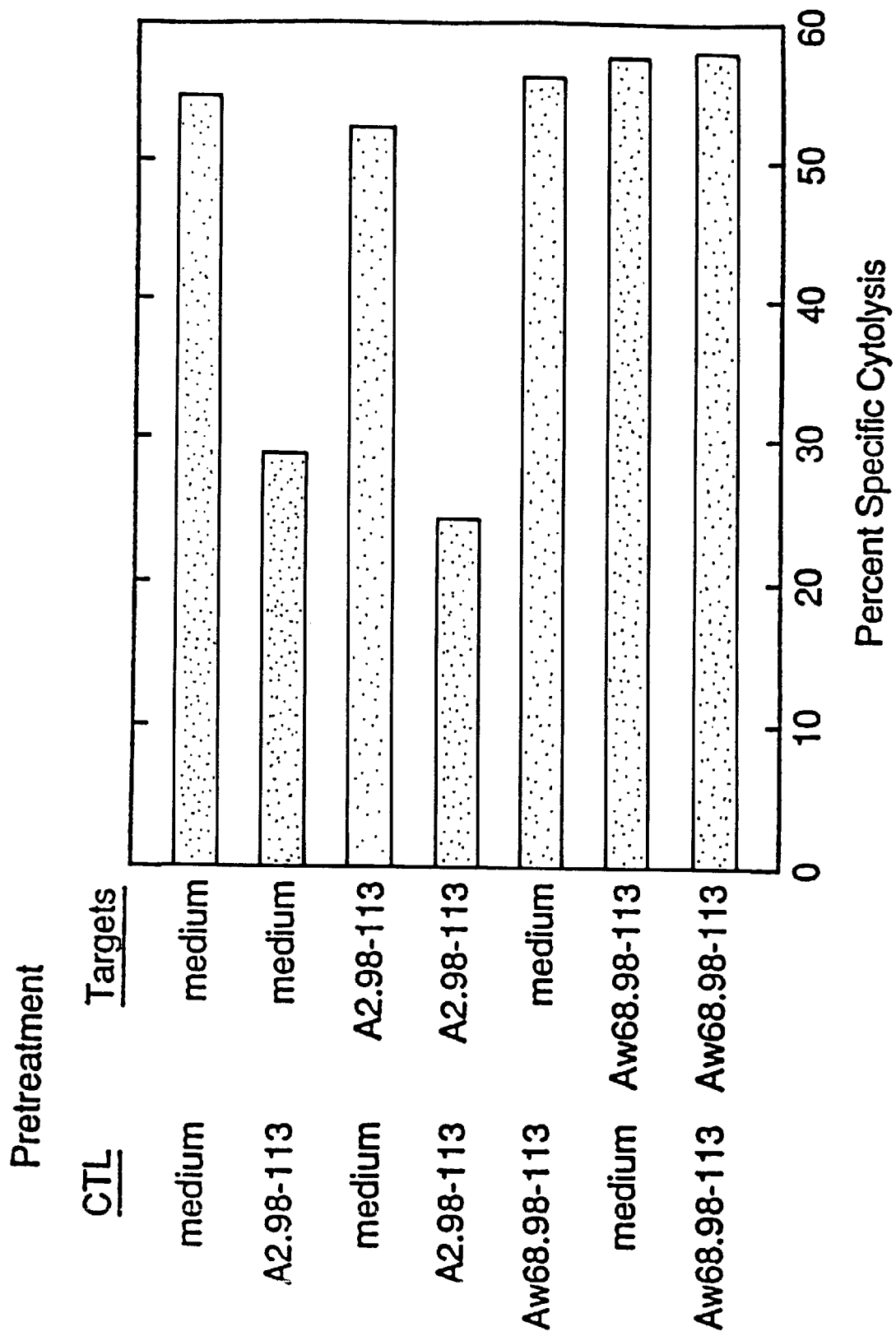
FIG. 2 shows the effect of pretreatment of CTL and of target cells on the inhibition of cytolysis by HLA-A2 specific CTL.

The results are presented in FIG. 2, where it may be seen that lysis was inhibited when the CTL, but not the target cells, were pretreated with A2.98-113. Inhibitory effects were not observed when CTL or target cells were pretreated with the control peptide, Aw68.98-113.

Example 6

Mechanism of Inhibition of CTL by A2.98-113
Effect on CTL Viability

To determine whether CTL were inhibited due to their autolysis induced by A2.98-113, either $^{51}$Cr-labeled CTL-A2 cells or unlabeled CTL-A2 cells were incubated with the peptide for 6 hours at 37° C. in complete medium. During the 6 hour incubation there was no detectable decrease in cell viability as judged by exclusion of trypan blue or by $^{51}$Cr-release (results not shown).

Example 7

Mechanism of Inhibition of CTL by A2.98-113
Effect on Release of Granules Containing Serine Esterase The effect of A2.98-113 on release of granules containing serine esterase during cytolysis of target cells by CTL was determined as follows.

The specificity of release was determined by incubating 3×10$^5$ HLA-A2 specific CTL with JY cells (HLA-A2; B7; Dr4,6) or IBW4 cells (HLA-A3; B35; DR1) for 2 hours in V bottom microtiter wells. The ratios of CTL:target cells were 1:0.01, 1:0.05, 1:0.10, 1:0.5, and 1:1. After the incubation, the plates were spun at 1000 RPM for 2 minutes, and the supernatant was assayed for serine esterase activity essentially as described in Young et al., Cell 47:183 (1986), which is hereby incorporated herein by reference. The reaction mixtures consisted of 20 μl of supernatant plus 200 μl of substrate (2×10$^{-4}$M N-benzyloxycarbonyl-L-lysine thiobenzyl ester, 2.2×10$^4$M nitrobenzoic acid, 0.1M Tris- HCl, pH 8.0). After 30 min. at 37° C., the absorbance was determined at 410 nm. Total serine esterase activity was determined by substituting 0.01% Triton X-100 for stimulator cells. The results, shown in FIG. 3A, indicate that release of the granules occurred when the HLA-A2 specific CTL were incubated with JY cells (closed circles), but not when the HLA-A2 specific CTL were incubated with IBW4 cells (closed squares).

The effect of peptide A2.98-113 on release of granules containing serine esterase was determined in a similar fashion, except that the HLA-A2 specific CTL were preincubated with 100 μg of peptide, either A2.98-113 or Aw68.98-113, or with only complete medium, for 30 min. at 37° C. prior to the addition of JY target cells at ratios of CTL:target cells of 1:0.01, 1:0.05, 1:0.1, 1:0.5 and 1:1.

Figure 3:
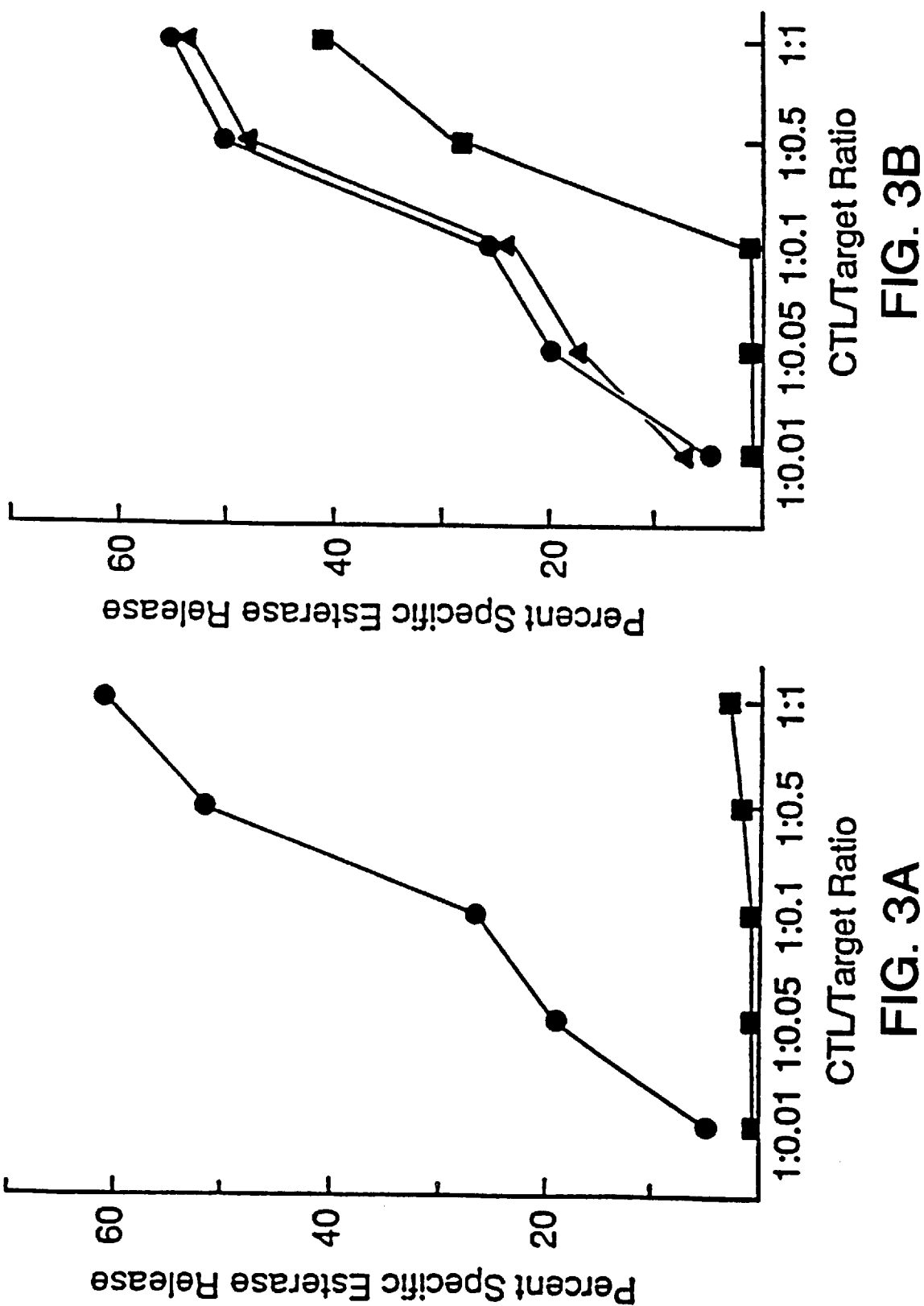
FIGS. 3A and B show the effect of peptide A2.98-113 on release of granules containing serine esterase during cytolysis of target cells by CTL.
Figure 5A:
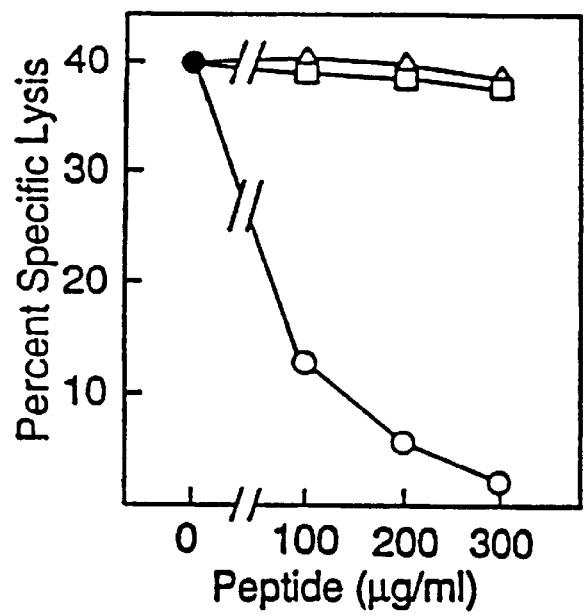
FIGS. 5A, B, C, and D show the effect of peptides from different HLA-A2 epitopes on cytolysis of target cells by CTL of different specificities.
Figure 5B:
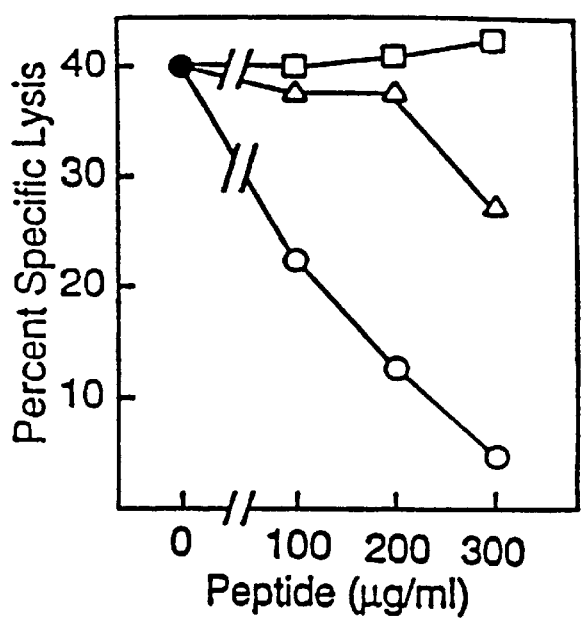
Figure 5C:
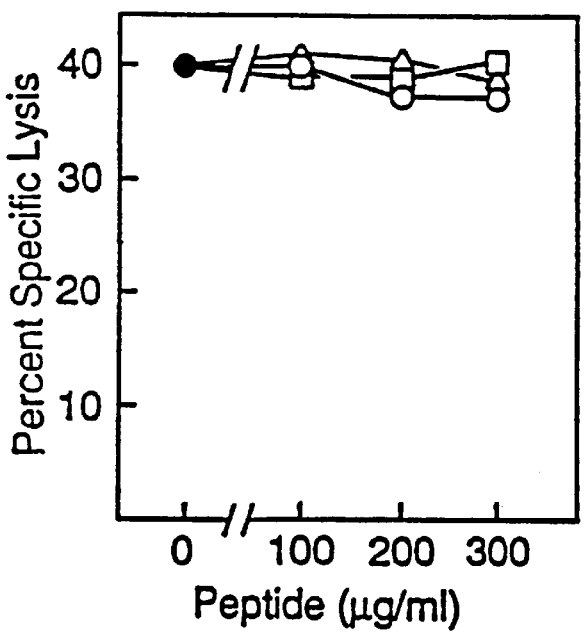
Figure 5D:
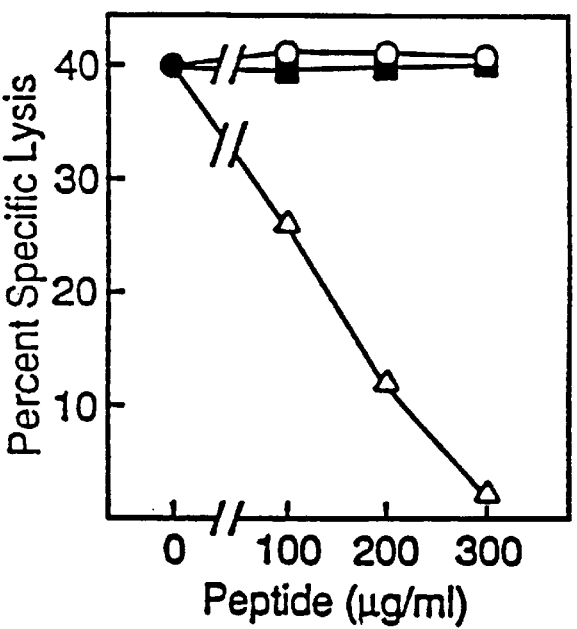

As seen in FIG. 3B, complete inhibition of esterase release was seen with 100 μg/ml of A2.98-113 at an effector-to-target ratio of 1:0.1 (closed squares). The control peptide Aw68.98-113 had no effect on esterase release (closed triangles), since release in this case was equal to that obtained with control cells preincubated with complete medium (closed circles).

These results, in conjunction with those in Example 5 indicate that the A2.98-113 peptide blocks events which occur early in T cell activation by binding directly to the CTL. This binding may be to the antigen receptor.

Example 8

Isolation of CTL Specific for the Epitope Shared by HLA-A2 and HLA-B17, for HLA-B17, and for HLA-A2

CTL with the various specificities were derived from the peripheral blood lymphocytes of a normal donor (HLA-A3; B7; DR6) essentially as described by Clayberger et al. (1985), supra. For CTL specific for the epitope shared between HLA-A2 and HLA-B17, the cells were stimulated in primary culture with the irradiated (10,000R) B-lymphoblastoid cell line Mag (HLA-A26,33; B17,51) and cloned using the SB cell line (HLA-A1,2; B17,44; DR2,6) as stimulators. CTL specific for B17 were derived from the same primary culture, but were cloned using the SH cell line (HLA-A3,w33; B7,17(w57)) as stimulators. HLA-A2 specific CTL were derived from cell stimulated in primary culture with the JY cell line and cloned using the Herluff cell line (HLA-A2; B12,35; DR4,7) as stimulators. The fine specificity of these CTL clones was assessed using a panel of 11 targets expressing HLA-B17, 8 targets expressing HLA-A2 and 15 targets with unrelated HLA molecules. Multiple clones of the desired specificities were obtained. An individual clone which caused cytolysis of both HLA-A2 type target cells and HLA-B17 type target cells was designated clone A2/B17. The cytolysis of target cells of clone A2/B17 was inhibited by antibody MA2.1. A second clone, which lysed all HLA-B17 target cells but no others was designated B17. A third clone, which lysed all HLA-A2 target cells but no others was designated CTL-A2.

The target specificity of clone A2/B17 and the finding that cytolysis by this clone was blocked by monoclonal antibody MA2.1 indicates that cells of clone A2/B17 recognize the epitope shared by HLA-A2 and HLA-B17.

Example 9

The Effect of Peptides from Different HLA-A2 Epitopes on Cytolysis of Target Cells by CTL of Different Specificities Examples 2–7, supra, have involved the effects of peptides derived from the region around tryptophan 107 in the $\alpha_2$ domain. This residue, which is on a bend between two strands of β pleated sheet (Bjorkman et al., (1987), supra), is critical for a major serologic epitope of HLA-A2. Salter et al., *J. Exp. Med.* 166:283 (1987); Layet et al., *J. Immunol.* 138:2197 (1987).

Another important epitope involves residues 62–65 of the α helical region of the a, domain. Bjorkman et al., supra. This epitope was originally defined by the monoclonal antibody MA2.1 (McMichael et al., *Hum. Immunol.* 1:121 (1980)), and is shared by all known subtypes of HLA-A2 and HLA-B17 (Ways and Parham, *Biochem. J.* 216:423 (1983)). A comparison of the amino acid sequence of HLA-A2 and HLA-B17 and eight other HLA-A,B,C proteins showed that only the glycine residue at position 62 is conserved, suggesting that this residue contributes to a shared determinant (Ways et al., *J. Immunol.* 137:217 (1986)).

Peptides derived from the above two regions were examined for their inhibitory effect on cytolysis of target cells by CTL with different HLA specificities, i.e., those of clone A2/B17, clone CTL-A2, and clone B17 (see Example 8, supra). CTL were incubated with the following peptides: A2.56-69, Aw68.56-69, A2.98-113, or Aw68.98-113.

Figure 4:
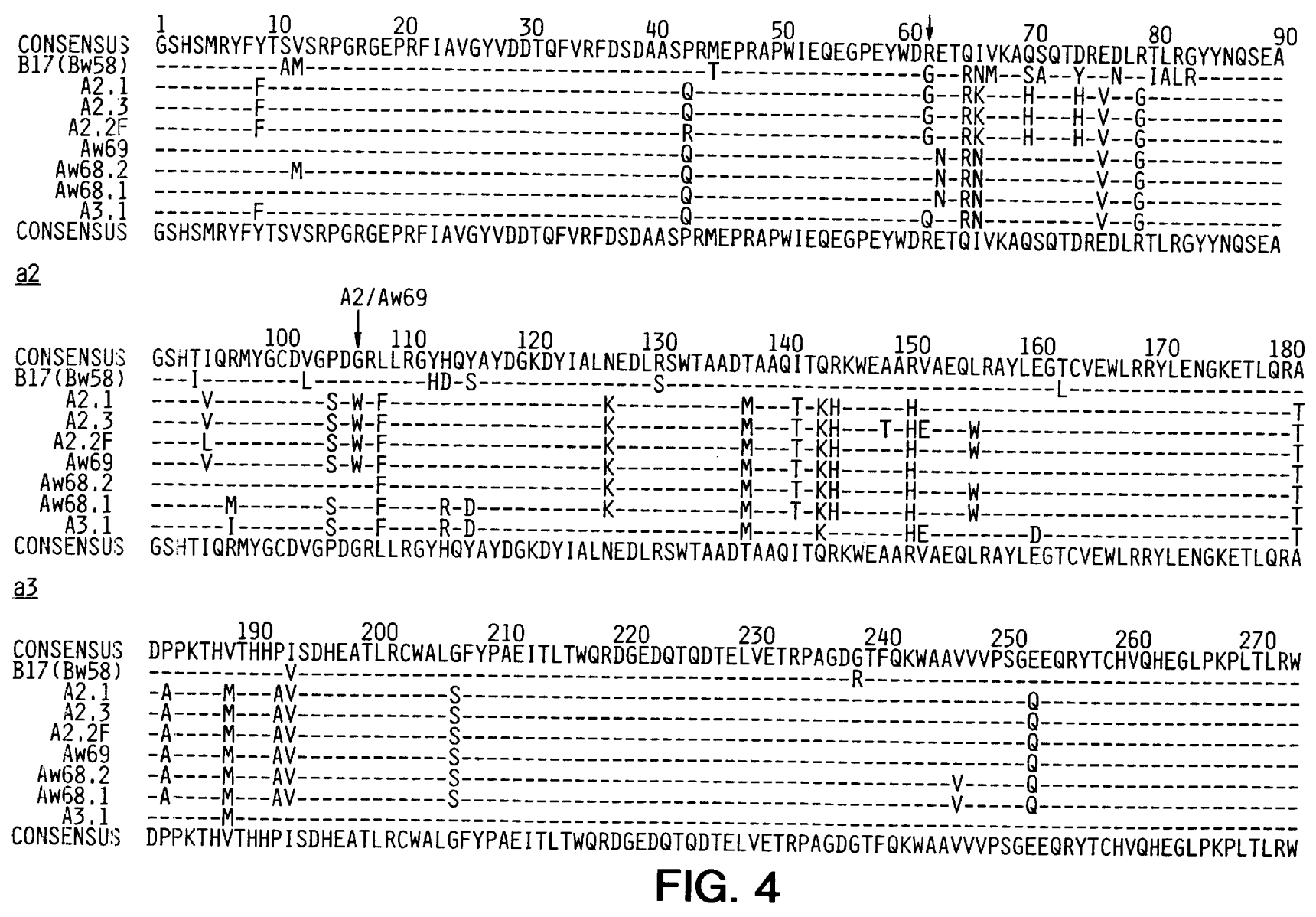

The epitopes studied and peptides used in the study are shown in FIG. 4, where the protein sequences in the three extracellular domains ($\alpha_1$, $\alpha_2$ and $\alpha_3$) of eight HLA-A,B molecules are shown using the standard one letter amino acid code. The sequence of HLA.Bw58 subtype of HLA-B17 is from Ways et al., *J. Biol. Chem.* 260:11924 (1985), that of HLA-A3.1 is from Strachen et al., *EMBO J.* 3:887 (1984), and the remaining sequences of the HLA-A2/28 family are from Holmes et al., *J. Immunol.* 139:936 (1987). Peptides A2.56-69 and Aw68.56-69, and A2.98-113 and Aw68.98-113, which are derived from $\alpha_1$ and $\alpha_2$, respectively, are indicated by cross-hatching. The two residues found to be critical for the epitopes shared by subtypes of HLA-A2 and HLA-B17 (glycine 62) and subtypes HLA-A2 and HLA-Aw69 (tryptophan 107) are indicated by stippling and the vertical arrows. The consensus sequence is derived from a total of 23 HLA-A,B,C sequences.

The CTL were incubated with peptides at concentrations of 100 μg/ml, 200 μg/ml, or 300 μg/ml. Control samples were incubated in the absence of peptide. The final molar concentrations of peptides used in the assay at 100 μg/ml were $4.9 \times 10^{-5}$M for A2.98-113: $5.2 \times 10^{-5}$M for Aw68.98-113; $5.9 \times 10^{-5}$M for A2.56-69; and $5.9 \times 10^{-5}$M for Aw68.56-69. The CTL cells were incubated with the peptides for 20 min. prior to the addition of $10^3$ $^{51}$Cr-labeled T7529 cells (HLA-Aw33; B17(w58); DR6) or JY cells (HLA-A2; B17; DR4,6). In all cases, the effector-to-target ratios were 1:1.

The results on cytotoxicity, as measured by $^{51}$chromium release from the target cells, is shown in FIG. 5. FIGS. 5A and 5B show the results of the effects of the peptides on cells of clone A2/B17; FIG. 5C shows the effects on cells of clone B17, and FIG. 5D on CTL-A2. The peptides are indicated as follows: (open circles) A2.56-69; (open squares) Aw68.56-69; (open triangles) Aw.98-113; and (closed squares) Aw68.98-113. Peptide A2.56-69, which encompasses the shared serologic epitope, specifically inhibited the killing of both HLA-A2 and HLA-B17 expressing target cells by clone A2/B17 cells. In contrast, this peptide had no effect upon the lysis of HLA-B17 expressing cells by clone B17 cells. Clone A2/B17 cells were not inhibited by a peptide derived from residues 56–69 of HLA-Aw68.1, or by a series of unrelated peptides. The A2.98-113 peptide did not affect the lysis of HLA-B17 expressing targets by clone A2/B17 cells, but some inhibition was observed at high concentrations with HLA-A2 expressing targets. This difference indicates that the epitopes of HLA-A2 and HLA-B17 recognized by clone A2/B17 cells are not precisely the same.

These results show that the capacity of peptides to inhibit alloreactive CTL is not restricted to the region involving residues 101–108 of the $\alpha_2$ domain, and that they may be derived from a second epitope of HLA-A2.

The discrepancy of the results achieved with peptide A2.56-69 using clone A2/B17, and those with the PWSB cell line (see Table 2) with respect to the inhibitory effect of this peptide may be explained by the polyclonal nature of the PWSB cells. That is, the PWSB line probably is a mixture of CTL's including individual clones specific for HLA-A2 or HLA-B17.

Example 10

Sensitization of Target Cells to CTL Caused by a HLA-2 Derived Polypeptide

Clone A2/B17 was incubated with peptide A2.56-69 and $^{51}$Cr-labeled target cells at an effector-to-target ratio of 5:1 for 5 hours, after which $^{51}$chromium released was measured. The concentrations of peptide were 10, 30, 100, and 300 μg/ml. The results of the effect of peptide on the percent of specific lysis of the target cells by clone A2/B17 cells are presented in FIG. 6. The target cells were: (closed square), IBW4 (HLA-A3; B35; DR1); (closed triangle), LB (HLA-Aw68.1; B40, DR6); (closed circle), Pally (HLA-Aw68.2, 26; B14,38; DR1,4), or (open diamond), IDF (HLA-Aw69, 26; B15, 38, DR5).

In the absence of peptide, clone A2/B17 cells do not lyse targets expressing HLA-Aw69, HLA-Aw68.1, and HLA-Aw68.2 (data not shown). The inability of clone A2/B17 cells to lyse these targets is due to the differences in the critical residues around position 62 from those found in HLA-A2 and HLA-B17. However, when peptide A2.56-69 was included in the cytotoxicity assay, there was significant lysis of HLA-Aw69 expressing targets by A2/B17 cells (FIG. 5). In contrast, targets expressing HLA-Aw68.1, HLA-Aw68.2, or the unrelated HLA-A3 molecule were not lysed.

Lysis of HLA-Aw69 cells by clone A2/B17 cells in the presence of peptide A2.56-69 was blocked by monoclonal antibody DR11-351, which only binds to the HLA-Aw69 of the target cell. In contrast, the monoclonal antibody MA2.1 did not inhibit lysis (results not shown). MA2.1 binds to the epitope of HLA-A2 and HLA-B17 formed by residues 56–69, but does not bind to the HLA-Aw69 or peptide A2.56-69. These results demonstrate the involvement of the HLA-Aw69 molecule in the sensitization by peptide A2.56-69.

The addition of A2.98-113 peptide to B cell lines which do not express HLA-A2 did not cause sensitization to lysis when target cells expressing a variety of HLA molecules were used. This was true even though a wide range of peptide concentrations (0.1 to 300 μg/ml were used.)

In binding A2.56-69, the HLA-Aw69 molecule is able to present an epitope that mimics the native structure of HLA-A2. That HLA-Aw69 but not other members of the HLA-A2/28 family can be sensitized is of interest. HLA-Aw69 is a recombinant molecule having $\alpha_1$ derived from HLA-Aw6B and $\alpha_2$ and $\alpha_3$ derived from HLA-A2.1 (Holmes and Parham, *EMBO J.* 4:2849 (1985)). Thus, HLA-2.1 and HLA-Aw69 differ by only 6 amino acids, all residing in the $\alpha_1$ domain and three of which are present in the A2.56-69 peptide.

Example 11

Locus of Peptide Interaction in Sensitization

To assess whether sensitization resulted from peptide interaction with the CTL or the target, cells were pretreated with A2.56-69, washed and then tested for cytolysis. More specifically, 1×10$^6$ clone A2/B17 cells or $^{51}$Cr-labeled IDF (HLA-Aw69,26; B18,38; DR5) were incubated with 100 μg of peptide or medium for 30 min. at 37° C., washed three times, and cytotoxicity as determined by $^{51}$chromium release was measured.

As seen from the results presented in FIG. 7, target cells expressing HLA-Aw69 were lysed when the targets, but not the CTL, were pretreated with A2.56-69.

Example 12

Effect of Peptide A2.56-69 on Release of Granules Containing Serine Esterase

The effect of peptide A2.56-69 on the release of granules containing serine esterase during co-culture of A2/B17 cells with HLA-Aw69 expressing cells may be performed essentially as described in Example 7, supra, except that the CTL are from clone A2/B17, the target cells are those expressing HLA-Aw69, and the cells are co-cultured in the absence or presence of peptide A2.56-69.

Example 13

Effect of a Variety of HLA Peptides of Amino Acids 60–84 and HLA-B 2702/05.145-169 on Lysis These peptides were synthesized and had the following sequence

| | |
|---|---|
| HLA-B2702.60–84 | WDRETQICKAKAQTDRENLRIALRY Seq. ID No: 6 |
| HLA-B2705.60–84 | WDRETQICKAKAQTDREDLRTLLRY Seq. ID No: 21 |
| HLA-BW46.60–84 | WDRETQKYKRQAQTDRVSLRNLRGY Seq. ID No: 7 |
| HLA-BW62.60–84 | WDRETQISKTNTQTYRESLRNLRGY Seq. ID No: 8 |
| HLA-A2.1.60–84 | WDGETRKVKAHSQTHRVDLGTLRGY Seq. ID No: 16 |
| HLA-B2702/05.145–169 | RKWEAARVAEQLRAYLEGECVEWLR Seq. ID No: 22 |
| HLAB88.60–84 | WDRNTQICKTNTQTYRENLRIALRY Seq. ID No: 23 |

The effect of the above sequences on lysis of long-term CTL specific for HLA-A2, -B2705, -Bw46, -Bw62, and -Cw4 was determined as described in Examples 2 and 3, and also included CTL specific for HLA-B27 and the HLA-Cw4. None of the peptides inhibited or enhanced lysis with the exception of the B2702.60-84 peptide. This peptide blocked lysis by all CTL, regardless of their HLA specificity. This effect was due to interaction with the CTL and not the target cell as shown by pre-treatment experiments (as in Example 5).

These peptides were tested for effects on the differentiation of CTL from CTL precursors in limiting dilution assay. The procedure was modified from Skinner and Marbrook (*J. Exp. Med.* 143:1562; 1976) as follows: PBL from normal HLA-typed donors were purified over Ficoll-Hypaque and co-cultured in round bottom microtiter wells with irradiated (10,000 R) EBV transformed B-lymphoblasts expressing the HLA allele of interest. Responder PBL were added at 3000, 6000, 10000 and 30000 cells per well while stimulators were added at 6000 cells per well. 20-4 replicates were set up for each concentration of responder cells in RPMI-1640 medium supplemented with 10% fetal bovine serum plus L-glutamine. Plates were incubated for six days in a 5% $CO_2$/95% air humidified incubator at which time the contents of each well were mixed by pipetting five times with a multi-channel pipette. Fifty microliter aliquots were transferred to the V-bottom microtiter wells to which 1000 $^{51}Cr$ labeled targets of known HLA type were then added. Lysis was determined in a four-hour cytotoxicity assay (Example 2). Wells were designated positive if specific lysis was >10%. CTL precursor frequency was determined by linear regression analysis using a computer program.

The B2702.60-84, Bw46.60-84 and Bw62.60-84 peptides all blocked the differentiation of CTL, whereas the other peptides had no effect.

Effect of Peptides Corresponding to HLA Regions on CTL Precursor Frequency as Determined by Limiting Dilution Analytis

| Peptide | 1/CTL Precursor Frequency |
| --- | --- |
| B2705.60-84 | 164,245 |
| B2702.60-84 | 3,349,990 |
| B38.60-84 | 3,334,937 |
| A2.160-84 | 164,245 |
| Bio46.60-84 | 2,995,400 |
| Bio62.60-84 | 2,995,400 |
| B27.145-169 | 164,245 |

PBL from a normal donor (HLA-A3; B-7, 38; Cw4; DR4,6) were cultured with ty (HLA-A2; B7; DR4,6) or HOM2 (HLA-A3; B27) in the presence of 10–100 μg/ml peptide. After 6 days, lysis was tested on $^{51}Cr$-labeled CIR cells expressing either HLA-A2.5 or HLA-B2705. Results are shown for HLA-A2 specific lysis but similar results were obtained for HLA-B27 specific lysis.

The effect was not allele specific since the differentiation of CTL specific for a number of different HLA molecules was inhibited. None of the peptides affected Class II restricted responses, including mixed lymphocyte responses and mitogen induced proliferation.

PBL from normal donors were cultured at 5×10⁵ cells/round bottom microtiter well in RPMI-1640 supplemented with 10% fetal bovine serum and L-glutamine. Cultures were supplemented with either 5×10³ irridiated (10,000 R) PBV transformed B lymphoblasts or 10 μg/ml phytahemagglutinin P (PHA-P). Cells were incubated at 37° C. for 3 days for PHA-P and 5 days for alloantigen at which point $^3H$-thymidine was added (2 μli/well). After 16 hours wells were harvested and $^3H$-thymidine incorporation determined by sciutillation counter.

Example 14

Effect of Truncated Sequences on Lysis and Differentiation

Since the B2702.60-84 and B2705.60-84 peptides differed by only 3 amino acids, additional peptides were prepared to investigate the effect of these differences. Three additional peptides were synthesized:

| HLA-B2702.75-84 | RENLRIALRY Seq. ID No: 24 |
| --- | --- |
| HLA-B2705.75-84 | REDLRTLLRY Seq. ID No: 25 |
| HLA-B2702/05.60-69 | WDRETQICKA Seq. ID No: 26 |

Following the procedures described in Example 13, the peptide corresponding to residue 60–69 of HLA-B2702/05 had no effect on the assays described above. The peptide corresponding to residue 75–84 of HLA-B2702 blocked all Class I specific CTL responses, whereas the peptide corresponding to the same region of HLA-B2705 did not.

To determine which residue(s) mediated the inhibitory effects, 3 more peptides were synthesized in which single amino acid changes were introduced at residues 77, 80 and 81 to convert the B2702 sequence into the B2705 sequence at that position. The B2702.75-84(D) and B2702.75-84(L) peptides still blocked lysis by existing CTL and differentiation of pre-CTL while the B2702.75-84(T) peptide had no inhibitory activity. Thus, the isoleucine at position 80 is required for inhibition.

| HLA-B2702.75-84(D) | REDLRIALRY Seq. ID No: 3 or 27 |
| --- | --- |
| HLA-B2702.75-84(T) | RENLRTALRY Seq. ID No: 28 |
| HLA-B2702.75-84(L) | RENLRILLEY Seq. ID No: 29 |

It was also found by the following assay that B2702.60-84, B38.60-84 and B2702.75-84 when pre-bound to plastic caused cells to bind. None of the other peptides were found to have this effect. However, when the B2702.60-84 peptide was conjugated to bovine serum albumin or to beads via the cysteine at residue 67, the blocking effect and the ability to bind cells to plastics were lost.

The plastic binding procedure was as follows: peptide (100 μg/ml) was dissolved in PBS and 50 μl was added to round bottom microtiter wells or 5–10 μl to petri dishes. After 60 minutes at 37° C. or overnight at 4°, the solution was removed and the plates washed twice in RPMI-1640 supplemented with 10% fetal bovine serum. Cells were added and incubated at 4° for 30 minutes. Binding to petri dishes was determined by inspecting the dishes under a microscope following gentle agitation. Binding to microtiter wells was determined after centrifugation at 500 rpm for 3 minutes. Cells which did not bind formed a small pellet at the bottom of the well whereas cells that did bind did not form a pellet.

Binding occurred equally well at 4°, 25°, or 37° and was not dependent on exogenously added divalent cations since binding was observed in medium containing EDTA. However, if cells were preincubated with 1% $NaN_3$ or fixed with paraformaldehyde, no binding was observed, indicating that viable cells and most likely generation of ATP were required.

It is evident from the above results that fragments of the polymorphic regions of Class I MHC antigens can find use in the modulation of CTL activity and other purposes associated with binding of the Class I MHC antigens and proteins which bind to such antigens. The subject compositions may be used for inhibiting CTL toxicity against a target, such as in the case of transplantation, where such activity is undesired. Alternatively, the subject compositions can be used to direct molecules to CTL. Alternatively, the subject compositions may be conjugated to an antigen of interest to activate CTL to lyse cells carrying antigens other than those recognized by the CTL and thus may induce CTL to lyse cells carrying antigens cryptic to the host, as in parasitic diseases and neoplasia. The subject compounds may find use in viral studies to determine MHC sequences associated with restriction of T-cells in the case of viral infection. The peptides may also be used to identify T-cells which specifically bind to the peptides in the context of a particular MHC antigen. Thus, one may isolate subsets of CTL, identify the presence of particular CTL, which may be useful in predicting the success of an allogeneic transplant or whether therapeutic measures are warranted, in investigating tolerization or holes in the repetoire, and the detection of autoimmune disease.

The generic blocking capability of peptide compounds would allow their general use with all HLA types, particularly with organ transplant recipients. The specific effect of the peptide compounds on the generation of CTL but not on lysis by existing CTL allows for sparing memory responses, while blocking the development of donor specific responses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A peptide agent that can inhibit CTL activity when said agent is contacted with said CTL, wherein said peptide consists of 30 amino acids or less in length and wherein said peptide comprises the amino acid sequence:

$RX_1X_2LX_3X_4X_5X_6X_7Y$ (Seq. ID No:1)

wherein $X_1$ is selected from the group consisting of E and V;

$X_2$ is selected from the group consisting of D, S and N;

$X_3$ is selected from the group consisting of R and G $X_4$ is selected from the group consisting of I and N;

$X_5$ is selected from the group consisting of L and A;

$X_6$ is selected from the group consisting of R and L; and $X_7$ is selected from the group consisting of G and R wherein said peptide agent can inhibit CTL activity in a non-allele-specific manner.

2. The peptide of claim 1 wherein the formula $RX_1X_2LX_3X_4X_5X_6X_7Y$ (Seq. ID No:1) corresponds to residues 75–84 of the alpha-1 domain of an MHC Class I B-type allele.

3. The composition of claim 1, wherein the formula $RX_1X_2LX_3X_4X_5X_6X_7Y$ (Seq. ID No:1) corresponds to residues 75–84 of the alpha-1 domain of a human MHC Class I HLA-B allele.

4. The peptide of claim 3, wherein said human HLA-B allele is selected from the group consisting of the B2702, B38, B7, B62 and Bw46 allele.

5. The peptide of claim 4 wherein said human HLA-B allele is selected from the group consisting of the B2702 and B7 allele.

6. The peptide of claim 1 wherein said peptide agent consist of an amino acid sequence selected from the group consisting of:

RENLRILLRY Seq. ID No:2;
REDLRIALRY Seq. ID No:3;
RESLRNLRGY Seq. ID No:4;
RVSLRNLRGY Seq. ID No:5;
WDRETQICKAKAQTDRELRIALRY Seq. ID No:6;
WDRETQKYKRQTDDRVSLRNLRGY Seq. ID No:7; and
WDRETQISKTNTQTYRESLRNLRGY Seq. ID No:8.

7. The compound of claim 1 covalently attached to a detectable moiety.

8. The compound of claim 1 attached to a solid support.

* * * * *

UNITED STATES PATENT AND TRADEMARK OFFICE
CERTIFICATE OF CORRECTION

PATENT NO. : 5,888,512
DATED : March 30, 1999
INVENTOR(S) : Carol A. CLAYBERGER *et al.*

It is certified that error appears in the above-identified patent and that said Letters Patent is hereby corrected as shown below:

In column 1, line 12, before "Introduction", please insert:
--This invention was made with Government support under Grant No. NIH 5 R01 AI22039 awarded by the National Institutes of Health. The Government has certain rights in this invention.--

Signed and Sealed this

Fifth Day of September, 2000

Attest:

Q. TODD DICKINSON

*Attesting Officer*     *Director of Patents and Trademarks*

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( i i i ) HYPOTHETICAL: NO ( v ) FRAGMENT TYPE: internal ( i x ) FEATURE:
        ( A ) NAME/KEY: Peptide
        ( B ) LOCATION: 1..10
        ( D ) OTHER INFORMATION: /product="OTHER"
          / note= "Xaa1 is E or V, Xaa2 is D, S, or N, Xaa3 is R or
          G, Xaa4 is I or N, Xaa5 is L or A, Xaa6 is R or L, Xaa7
          is G or L"

( x i ) SEQUENCE DESCRIPTION: SEQ ID NO:1:

```
Arg  Xaa  Xaa  Leu  Xaa  Xaa  Xaa  Xaa  Xaa  Tyr
1                     5                          10
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:2:

```
Arg  Glu  Asn  Leu  Arg  Ile  Leu  Leu  Arg  Tyr
1                     5                          10
```

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( i x ) FEATURE:

(A) NAME/KEY: Peptide
(B) LOCATION: 3..14
(D) OTHER INFORMATION: /product="OTHER"
/ note= "X1 IS I, L OR V, X2 IS D, E, I,L OR V, X3 IS K,
N, Q OR R, X4 IS H, N, Q, S OR T, X5 IS D, E, N OR Q,
X6 IS I, L, S, T OR V, X7 IS I, L, N OR V, X8 IS I, L,
S, T AND V, X9 IS K, N, Q OR R"

(xi) SEQUENCE DESCRIPTION: SEQ ID NO:3:

```
Arg  Glu  Asp  Leu  Arg  Ile  Ala  Leu  Arg  Tyr
1                   5                        10
```

(2) INFORMATION FOR SEQ ID NO:4:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:4:

```
Arg  Glu  Ser  Leu  Arg  Asn  Leu  Arg  Gly  Tyr
1                   5                        10
```

(2) INFORMATION FOR SEQ ID NO:5:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:5:

```
Arg  Val  Ser  Leu  Arg  Asn  Leu  Arg  Gly  Tyr
1                   5                        10
```

(2) INFORMATION FOR SEQ ID NO:6:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (v) FRAGMENT TYPE: internal (xi) SEQUENCE DESCRIPTION: SEQ ID NO:6:

```
Trp  Asp  Arg  Glu  Thr  Gln  Ile  Cys  Lys  Ala  Lys  Ala  Gln  Thr  Asp  Arg
1                   5                        10                       15

Glu  Leu  Arg  Arg  Ile  Ala  Leu  Arg  Tyr
                    20                  25
```

(2) INFORMATION FOR SEQ ID NO:7:

(i) SEQUENCE CHARACTERISTICS:
        (A) LENGTH: 24 amino acids
        (B) TYPE: amino acid
        (C) STRANDEDNESS:
        (D) TOPOLOGY: linear (ii) MOLECULE TYPE: peptide (v) FRAGMENT TYPE: internal (x i) SEQUENCE DESCRIPTION: SEQ ID NO:7:

```
Trp Asp Arg Glu Thr Gln Lys Tyr Lys Arg Gln Thr Asp Asp Arg Val
1               5                   10                  15
Ser Leu Arg Asn Leu Arg Gly Tyr
            20
```

(2) INFORMATION FOR SEQ ID NO:8:

(i) SEQUENCE CHARACTERISTICS:
        (A) LENGTH: 25 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO:8:

```
Trp Asp Arg Glu Thr Gln Ile Ser Lys Thr Asn Thr Gln Thr Tyr Arg
1               5                   10                  15
Glu Ser Leu Arg Asn Leu Arg Gly Tyr
            20                  25
```

(2) INFORMATION FOR SEQ ID NO:9:

(i) SEQUENCE CHARACTERISTICS:
        (A) LENGTH: 67 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO:9:

```
Xaa Gly Pro Glu Tyr Trp Asp Xaa Xaa Thr Xaa Xaa Xaa Lys Xaa Xaa
1               5                   10                  15
Xaa Gln Thr Xaa Arg Xaa Xaa Leu Xaa Xaa Xaa Xaa Xaa Xaa Tyr Tyr
            20                  25                  30
Asn Gln Ser Glu Ala Gly Ser His Xaa Xaa Gln Xaa Met Xaa Gly Cys
            35                  40                  45
Asp Xaa Gly Xaa Asp Xaa Arg Xaa Leu Arg Gly Xaa Xaa Gln Xaa Ala
        50                  55                  60
Tyr Asp Gly
65
```

(2) INFORMATION FOR SEQ ID NO:10:

(i) SEQUENCE CHARACTERISTICS:
        (A) LENGTH: 37 amino acids
        (B) TYPE: amino acid
        (C) STRANDEDNESS:
        (D) TOPOLOGY: linear (i i) MOLECULE TYPE: peptide (v) FRAGMENT TYPE: internal (x i) SEQUENCE DESCRIPTION: SEQ ID NO:10:

```
Gln Glu Gly Pro Glu Tyr Trp Asp Xaa Xaa Thr Xaa Xaa Val Lys Ala
1               5                   10                  15
```

```
Xaa  Ser  Gln  Thr  Xaa  Arg  Xaa  Xaa  Leu  Xaa  Xaa  Xaa  Xaa  Xaa  Tyr  Tyr
               20                  25                          30

Asn  Gln  Ser  Glu  Ala
               35
```

( 2 ) INFORMATION FOR SEQ ID NO:11:

( i ) SEQUENCE CHARACTERISTICS:
        ( A ) LENGTH: 19 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
Thr  Leu  Gln  Arg  Met  Tyr  Gly  Cys  Asp  Val  Gly  Ser  Asp  Trp  Arg  Phe
1                   5                        10                       15

Leu  Arg  Gly
```

( 2 ) INFORMATION FOR SEQ ID NO:12:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Met  Tyr  Gly  Cys  Asp  Val  Gly  Ser  Asp  Trp  Arg  Phe  Leu  Arg  Gly  Tyr
1                   5                        10                       15
```

( 2 ) INFORMATION FOR SEQ ID NO:13:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Met  Tyr  Gly  Cys  Asp  Val  Gly  Ser  Asp  Gly  Arg  Phe  Leu  Arg  Gly  Tyr
1                   5                        10                       15
```

( 2 ) INFORMATION FOR SEQ ID NO:14:

( i ) SEQUENCE CHARACTERISTICS:
        ( A ) LENGTH: 14 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:14:

```
Gly  Pro  Glu  Tyr  Trp  Asp  Gly  Glu  Thr  Arg  Lys  Val  Lys  Ala
1                   5                        10
```

( 2 ) INFORMATION FOR SEQ ID NO:15:

( i ) SEQUENCE CHARACTERISTICS:
        ( A ) LENGTH: 26 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:15:

```
Trp Asp Arg Glu Thr Gln Ile Cys Lys Ala Lys Ala Gln Thr Asp Arg
 1               5                  10                  15
Asn Xaa Leu Arg Xaa Xaa Leu Arg Tyr Tyr
             20              25
```

( 2 ) INFORMATION FOR SEQ ID NO:16:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:16:

```
Trp Asp Gly Glu Thr Arg Lys Val Lys Ala His Ser Gln Thr His Arg
 1               5                  10                  15
Val Asp Leu Gly Thr Leu Arg Gly Tyr
             20              25
```

( 2 ) INFORMATION FOR SEQ ID NO:17:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:17:

```
Arg Glu Asp Leu Arg Thr Leu Leu Arg Tyr
 1               5                  10
```

( 2 ) INFORMATION FOR SEQ ID NO:18:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:18:

```
Trp Asp Arg Glu Thr Gln Ile Cys Lys Ala
 1               5                  10
```

( 2 ) INFORMATION FOR SEQ ID NO:19:

( i ) SEQUENCE CHARACTERISTICS:
   ( A ) LENGTH: 30 amino acids
   ( B ) TYPE: amino acid
   ( C ) STRANDEDNESS:
   ( D ) TOPOLOGY: linear ( i i ) MOLECULE TYPE: peptide ( v ) FRAGMENT TYPE: internal ( x i ) SEQUENCE DESCRIPTION: SEQ ID NO:19:

Gly His Ser Thr Xaa Gln Arg Met Tyr Gly Cys Asp Val Gly Ser Glu
1               5                   10                  15

Xaa Arg Phe Leu Arg Gly Tyr His Gln Tyr Ala Tyr Asp Gly
           20                  25                  30

( 2 ) INFORMATION FOR SEQ ID NO:20:

( i ) SEQUENCE CHARACTERISTICS:
       ( A ) LENGTH: 14 amino acids
       ( B ) TYPE: amino acid
       ( C ) STRANDEDNESS:
       ( D ) TOPOLOGY: linear ( i i ) MOLECULE TYPE: peptide ( v ) FRAGMENT TYPE: internal ( x i ) SEQUENCE DESCRIPTION: SEQ ID NO:20:

Gly Pro Glu Tyr Trp Asp Gly Glu Thr Arg Lys Val Lys Ala
1               5                   10

( 2 ) INFORMATION FOR SEQ ID NO:21:

( i ) SEQUENCE CHARACTERISTICS:
       ( A ) LENGTH: 25 amino acids
       ( B ) TYPE: amino acid
       ( C ) STRANDEDNESS:
       ( D ) TOPOLOGY: linear ( i i ) MOLECULE TYPE: peptide ( v ) FRAGMENT TYPE: internal ( x i ) SEQUENCE DESCRIPTION: SEQ ID NO:21:

Trp Asp Arg Glu Thr Gln Ile Cys Lys Ala Lys Ala Gln Thr Asp Arg
1               5                   10                  15

Glu Asp Leu Arg Thr Leu Leu Arg Tyr
           20                  25

( 2 ) INFORMATION FOR SEQ ID NO:22:

( i ) SEQUENCE CHARACTERISTICS:
       ( A ) LENGTH: 26 amino acids
       ( B ) TYPE: amino acid
       ( C ) STRANDEDNESS:
       ( D ) TOPOLOGY: linear ( i i ) MOLECULE TYPE: peptide ( v ) FRAGMENT TYPE: internal ( x i ) SEQUENCE DESCRIPTION: SEQ ID NO:22:

Arg Lys Trp Glu Ala Ala Arg Val Ala Glu Gln Leu Arg Ala Tyr Leu
1               5                   10                  15

Glu Gly Glu Cys Cys Val Glu Trp Leu Arg
           20                  25

( 2 ) INFORMATION FOR SEQ ID NO:23:

( i ) SEQUENCE CHARACTERISTICS:
        ( A ) LENGTH: 25 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:23:

```
Trp Asp Arg Asn Thr Gln Ile Cys Lys Thr Asn Thr Gln Thr Tyr Arg
1               5                   10                  15
Glu Asn Leu Arg Ile Ala Leu Arg Tyr
            20              25
```

( 2 ) INFORMATION FOR SEQ ID NO:24:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:24:

```
Arg Glu Asn Leu Arg Ile Ala Leu Arg Tyr
1               5                   10
```

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:25:

```
Arg Glu Asp Leu Arg Thr Leu Leu Arg Tyr
1               5                   10
```

( 2 ) INFORMATION FOR SEQ ID NO:26:

( i ) SEQUENCE CHARACTERISTICS:
        ( A ) LENGTH: 10 amino acids
        ( B ) TYPE: amino acid
        ( C ) STRANDEDNESS:
        ( D ) TOPOLOGY: linear ( i i ) MOLECULE TYPE: peptide ( v ) FRAGMENT TYPE: internal ( x i ) SEQUENCE DESCRIPTION: SEQ ID NO:26:

```
Trp Asp Arg Glu Thr Gln Ile Cys Lys Ala
1               5                   10
```

( 2 ) INFORMATION FOR SEQ ID NO:27:

( i ) SEQUENCE CHARACTERISTICS:
        ( A ) LENGTH: 10 amino acids
        ( B ) TYPE: amino acid

```
          ( C ) STRANDEDNESS:
          ( D ) TOPOLOGY: linear ( i i ) MOLECULE TYPE: peptide ( v ) FRAGMENT TYPE: internal ( x i ) SEQUENCE DESCRIPTION: SEQ ID NO:27:

Arg  Glu  Asp  Leu  Arg  Ile  Ala  Leu  Arg  Tyr
    1                   5                        10

( 2 ) INFORMATION FOR SEQ ID NO:28:

( i ) SEQUENCE CHARACTERISTICS:
          ( A ) LENGTH: 10 amino acids
          ( B ) TYPE: amino acid
          ( C ) STRANDEDNESS:
          ( D ) TOPOLOGY: linear ( i i ) MOLECULE TYPE: peptide ( v ) FRAGMENT TYPE: internal ( x i ) SEQUENCE DESCRIPTION: SEQ ID NO:28:

Arg  Glu  Asn  Leu  Arg  Thr  Ala  Leu  Arg  Tyr
    1                   5                        10

( 2 ) INFORMATION FOR SEQ ID NO:29:

( i ) SEQUENCE CHARACTERISTICS:
          ( A ) LENGTH: 10 amino acids
          ( B ) TYPE: amino acid
          ( C ) STRANDEDNESS:
          ( D ) TOPOLOGY: linear ( i i ) MOLECULE TYPE: peptide ( v ) FRAGMENT TYPE: internal ( x i ) SEQUENCE DESCRIPTION: SEQ ID NO:29:

Arg  Glu  Asn  Leu  Arg  Ile  Leu  Leu  Glu  Tyr
    1                   5                        10
```